US006562790B2

(12) United States Patent
Chein

(10) Patent No.: US 6,562,790 B2
(45) Date of Patent: *May 13, 2003

(54) HORMONE THERAPY METHODS AND HORMONE PRODUCTS FOR ABATING CORONARY ARTERY BLOCKAGE

(76) Inventor: Edmund Y. M. Chein, 2825 Tahquitz Canyon Rd., Building A, Palm Springs, CA (US) 92262

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/498,792

(22) Filed: Feb. 5, 2000

(65) Prior Publication Data

US 2002/0065273 A1 May 30, 2002

(51) Int. Cl.$^7$ .......................... A61K 38/00; A61K 31/56
(52) U.S. Cl. ................. 514/21; 514/12; 514/2; 514/171; 514/177; 514/178; 514/182; 514/415
(58) Field of Search .............. 514/2, 21, 171, 514/177, 178, 182, 415, 12

(56) References Cited

U.S. PATENT DOCUMENTS

| | | |
|---|---|---|
| 4,727,041 A | 2/1988 | Aroonsakul |
| 4,791,099 A | 12/1988 | Aroonsakul |
| 4,897,389 A | 1/1990 | Aroonsakul |
| 4,898,856 A | 2/1990 | Aroonsakul |
| 4,898,857 A | 2/1990 | Aroonsakul |
| 4,902,680 A | 2/1990 | Aroonsakul |
| 5,017,470 A | 5/1991 | Aroonsakul |
| 5,391,381 A | 2/1995 | Wong et al. |
| 5,397,771 A | 3/1995 | Bechgaard et al. |
| 5,424,199 A | 6/1995 | Goeddel et al. |
| 5,434,146 A | 7/1995 | Labrie et al. |
| 5,550,107 A | 8/1996 | Labrie |
| 5,563,131 A | 10/1996 | Berliner et al. |
| 5,691,169 A | 11/1997 | Dalbage et al. |
| 5,691,325 A | 11/1997 | Sandyk |
| 5,855,920 A | 1/1999 | Chein |

OTHER PUBLICATIONS

Buerke et al. "Cardioprotective effect of insulin–like growth factor I in myocardial ischemia by reperfusion," 1995, Proc. Natl. Acad. Sci. USA, vol. 92, pp. 8031–8035.*
Isselbacher et al. 'Harrison's Principles of Internal Medicine,' 13th Edition, p. 81, McGraw Hill Inc., 1994.*
Advanced Medical Therapy: Human Growth Hormone Replacement Therapy In Adults, Edward M. Lichten, M.D., P.C. (1997).
PCT: WO 95/32991 (FAHY) See especially p. 4, line 4–14 (against claims 21–30).
"Administration of Human Somatotropin in Levodopa–Treated Patients With Parkinsonism" by Paul S. Papavasiliou et al., *Arch Neurol*, vol. 36, Oct. 1979.

"Long–Term Influence of Levodopa on Bone Mass and Growth Hormone in Postmenopausal Women with Parkinson's Disease" by H. Rico, et al., *Clinical Neuropharmacology*, vol. 10, No. 1, pp. 87–91, 1987.
"Clinical Studies of the Cholinergic Deficit in Alzheimer's Disease" by Bonnie M. Davis, MD, et al., *Journal of the American Geriatrics Society*, vol. 33, No. 11.
"Disturbances of Pituitary Function in Central Nervous System Disease" by Glenn T. Peake, MD, et al., *Medical Clinics of North America*, vol. 52, No. 2, Mar. 1968.
"Growth Hormone Response in Parkinson's Disease" by J.D. Parkes, et al., *The Lancet*, Feb. 28, 1976.
"Blood Levels of FSH, LH, TSH, And GH in Parkinsonian patients Before and During L–Dopa Treatment" by P.O. Lundberg, *Acta Neurol. Scandinav.*, vol. 48, pp. 427–432, 1972.
"Therapeutic Approaches in Parkinson's Disease: Possible Roles of Growth Hormone and Somatostatin" by George C. Cotzias, et al., *The Basal Ganglia*, 1976.
"Effects of Estrogen, Progestin and Combined Estrogen –Progestin Oral Contraceptive Preparations on Experimental Allergic Encephalomyelitis" by Barry G. Arnason et al., Boston, MA.
"Molecular Biology of Neurological and Psychiatric Disorders. I. Effect of Parkinsonism, Age, Sex and L–Dopa on Platelet Monoamine Oxidase" by E.A. Zeller, et al., *Journal of Neutral Transmission*, 39, pp. 63–77, 1976.
"Peliosis Hepatis Report of Nine Cases" by Tsutomu Karasawa, et al., *Acta Path. Jap.*, 29(3), pp. 457–469, 1979.
"Orale Ovulationshemmer—Indikationen und Komplikationen aus Neurologischer Sicht" by Sigrid Poser, *Fortschr. Neurol. Psychiat.*, 45, 1977.
"Contraccezione Orale e Sclerosi Multipla" by A. Ghezzi, et al., *Archivio per le Scienze Mediche*, 136, 1979.
"Estrogens and Extrapyramidal System" by P. Bedard, et al., *The Lancet*, Dec. 24 & 31, 1977.
"Etudes des Androgenes Plasmatiques Chez les Femmes Atteintes de Maladies Auto–Immunes" by M. Dougados, et al., *Revue du Rhumatisme*, 1984, 51(3), pp. 145–149.
"Observations in a Preliminary Open Trial of Estradiol Therapy for Senile Dementia–Alzheimer's Type" by Howard Fillit, et al., *Psychoneuroendocrinology*, vol. 11, No. 3, pp. 337–345, 1986.

(List continued on next page.)

Primary Examiner—Russell Travers
Assistant Examiner—Shengjun Wang
(74) Attorney, Agent, or Firm—Patrick F. Bright; Bright & Lorig

(57) ABSTRACT

Methods for abating coronary artery blockage in human subjects include administering a combination of natural hormones including human growth hormone with sufficient T3 thyroid supplement to maintain the body temperature of the subject at or above 97.6° F. upon awakening and at 98.7° F. or higher during afternoon hours. Testosterone, if any, administered to male subjects is in natural, gel form.

9 Claims, No Drawings

OTHER PUBLICATIONS

"Metabolic Effects of GH: A Rationale for Continued GH Treatment of GH–Deficient Adults After Cessation of Linear Growth" by A. Juul, et al., Department of Growth and Reproduction, University of Copenhagen, Denmark. *Horm Res* (Switzerland) 1995, 44 Suppl 3, pp. 64–72, ISSN 0301–0163, Journal Code GBI.

"Insulin–Like Growth Factor I Alters Peripheral Thyroid Hormone Metabolism in Humans: Comparison with Growth Hormone" by M.A. Hussain, et al., Division of Endocrinology and Metabolism, University Hospital of Zurich,Switzerland. *Eur J Endocrinol* (Norway) May 1996, 134 (5) pp. 563–567, ISSN 0804–4363, Journal Code BXU.

"Improved Final Height in Girls with Turner's Syndrome Treated with Growth Hormone and Oxandrolone" by K.O. Nilsson, et al., Department of Pediatrics, University Hospital Malmo, Sweden, *J. Clin Endocrinol Metab* (United States) Feb. 1996, 81(2) pp. 635–640, ISSN 0021–972X, Journal Code HRB.

"Insulin, Insulin–Like Growth Factor–Binding Protein–1, and Sex Hormone–Binding Globulin in Patients with Turner's Syndrome: Course Over Age in Untreated Patients and Effect of Therapy with Growth Hormone Alone and in Combination with Oxandrolene" by G. Haeusler, et al., Pediatric Department, University of Vienna, Austria. *J Clin Endocrinol Metab* (United States) Feb. 1996, 81(2) pp. 536–541, ISSN 0021–972X, Journal Code HRB.

"Growth Hormone Deficiency in Adults: Characteristics and Response to Growth Hormone Replacement" by S.A. Lieberman, et al., Department of Internal Medicine, University of Texas Medical Branch, Galveston, 77555–1060, USA. *J Pediatr* (United States) May 1996. 128 (5 Pt 2) pS58–60, ISSN 0022–3476, Journal Code JLZ.

"Effect of Anabolic Hormones and Insulin–Like Growth Factor–I on Muscle Mass and Strength in Elderly Persons" by W.J. Carter, et al., Memorial Veterans Hospital, Little Rock, Arkansas, USA. *Clin Geriatr Med* (United States) Nov. 1996, 11(4) p735–48, ISSN 0749–0690, Journal Code CLN.

"Screening for PIT1 Abnormality by PCR Direct Sequencing Method" by Y. Irie, et al., Department of Laboratory Medicine, Osaka University Medical School, Japan. *Thyroid* (United States) Jun. 1995, 5(3) p207–11, ISSN 1050–7256, Journal Code BJW.

"Trophic Factor Supplementation: Effect on the Age–Associated Changes in Body Composition" by R.S. Schwartz, et al., Division of Gerontology and Geriatric Medicine, Harborview Medical Center, Seattle, USA. *J Gerontol A Biol Sci Med Sci* (United States) Nov. 1995, 50 Spec No p151–6, ISSN 1079–5006, Journal Code CBA.

"Treatment of Growth Hormone–Deficient Adults with Recombinant Human Growth Hormones Increases the Concentration of Growth Hormone in the Cerebrospinal Fluid and Affects Neurotransmitters" by J.O. Johansson, et al., Department of Internal Medicine, University of Goteborg, Sweden. *Neuroendocrinology* (Switzerland) Jan. 1995, 61(1) p57–66, ISSN 0028–3835, Journal Code NY8.

"Adult Growth Hormone Deficiency" by J.O. Jorgensen, et al., Medical Department M (Endocrinology and Diabetes), Aarhus Kommunehospital, Denmark. *Horm Res* (Switzerland) 1994, 42(4–5) p235–41, ISSN 0301–0163, Journal Code GBI.

"Effects of Recombinant Human Growth Hormone on Metabolic Indices, Bodycomposition, and Bone Turnover in Health Elderly Women" by L. Holloway, et al., Aging Study Unit, Palo Alto Veterans Affairs Medical Center, California 94304. *J Clin Endocrinol Metab* (United States) Aug. 1994, 79(2) p470–9, ISSN 0021–972X, Journal Code HRB.

"Treatment of Growth Delay in Boys With Isolated Growth Hormone Deficiency" by A. Albanese, et al., Medical Unit, Institute of Child Health, London, UK. *Eur J Endocrinol* (Norway) Jan. 1994, 130(1) p65–9, ISSN 0804–4643, Journal Code BXU.

"Management of the Short Stature Due to Pubertal Delay in Boys" by L. Adan, et al., Pediatric Endocrinology Unit, Hopital et Faculte Necker–Enfants Malades, Paris, France. *J Clin Endocrinol Metab* (United States) Feb. 1994, 78(2) p478–82, ISSN 0021–972X, Journal Code HRB.

"Aging and Growth Hormone" by K.K. Ho, et al., Garvan Institute of Medical Research, St. Vincent's Hospital Sydney, Australia. *Horm Res* (Switzerland) 1993, 40(1–3) p80–6, ISSN 0301–0163, Journal Code GBI.

"Treatment of Adults with Growth Hormone (GH) Deficiency with Recombinant Human GH" by B.A. Bengtsson, et al., Department of Medicine, Sahlgrenska Hospital, Medical Faculty, University of Goteborg, Sweden. *J Clin Endocrinol Metab* (United States) Feb. 1993, 76(2) p309–17, ISSN 0021–972X, Journal Code HRB.

"Regulation of Growth Hormone Binding Protein in Man: Comparison of Gel Chomatography and Immunoprecipitation Methods" by K.K. Ho, et al., Garvan Institute of Medical Research, St. Vincent's Hospital, Sydney, Australia. *J Clin Endocrinol Metab* (United States) Feb. 1993, 76(2) p302–8, ISSN 0021–972 X, Journal Code HRB.

"Growth Hormone Therapy in Turner's Syndrome. Impact of Injection Frequency and Initial Bone Age" by C. Rongen–Westerlaken, et al., Department of Pediatrics, University of Utrecht, The Netherlands. *Am J Dis Child* (United States) Jul. 1992, 146(7) p817–20, ISSN 0002–922X, Journal Code 3GS.

"Nocturnal Thyrotropin Surge in Growth Hormone–Deficient Children" by G. Municchi, et al., Developmental Endocrinology Branch, National Institute of Child Health and Human Development, National Institutes of Health, Bethesda, Maryland 20892. *J Pediatr* (United States) Aug. 1992, 121(2) p214–20, ISSN 0022–3476, Journal Code JLZ.

"Effects of Human Growth Hormone in Men Over 60 Years Old" by Daniel Rudman, MD, et al., *The New England Journal of Medicine*, Jul. 5, 1990, vol. 323, No. 1.

"Restoring Ebbing Hormones May Slow Aging" by Jane E. Brody, *The New York Times*, Jul. 18, 1995.

"Life Extension Interview", *Life Extension*, Nov. 1996, p21–27.

"Brave Montel: How I'm Gonna Beat MS" by John Blosser, *National Enquirer*, Sep. 7, 1999.

"Multiple Sclerosis: The Immune System's Terrible Mistake" by Oeter Riskind, MD, PhD, *The Harvard Mahoney Neuroscience Institute Letter, On The Brain*, Fall 1996, vol. 5, No. 4.

"Evaluation of Progression in Multiple Sclerosis by Magnetic Resonance Imaging (MRI)", *National Institute of Neurological Disorders and Stroke (NINDS)*.

"Growth Factors and Myelin Regeneration in Multiple Sclerosis" by HD Webster, *Mult Scler*, Apr. 1997; 3(2); p113–20.

"Insulin–Like Growth Factor I Treatment Reduces Clinical Deficits and Lesion Severity in Acute Demyelinating Experimental Autoimmune Encephalomyelitis" by X. Liu, et al., *Mult Scler*, Apr. 1995, 1(1), p2–9.Effi "Chronic relapsing Experimental Autoimmune Encephalomyelitis: Effects of Insulin–Like Growth Factor–I Treatment on Clinical Deficits, Lesion Severity, Glial Responses, and Blood Brain Barrier Defects" by W. Li, et al., *J Neuropathol Exp Neurol*, May 1998, 57(5), p426–38.

"Insulin–Like Growth Factor–I Treatment Reduces Immune Cell Responses in Acute Non–Demyelinative Experimental Autoimmune Encephalomyelitis" by X. Liu, *J Neurosci Res*, Mar. 1997, 47(5), p531–8.

"Insulin–Like Growth Factor–I Given Subcutaneously Reduces Clinical Deficits, Decreases Lesion Severity and Up–Regulates Synthesis of Myelin Proteins in Experimental Autoimmune Encephalomyelitis" by DL Yao, *Life Sci*, 1996, 58(16), p1301–6.

"Insulin–Like Growth Factor–I Treatment Reduces Demyelination and Up–Regulates Gene Expression of Myelin–Related Proteins in Experimental Autoimmune Encephalomyelitis" by DL Yao, *Proc Natl Acad Sci USA*, Jun. 20, 1995, 92(13), p6190–4.

"A 48–Week (24–Week Baseline Followed by a 24–Week Treatment) Phase II Pilot Study of the Tolerability and Effect/Efficacy of Subcutaneously Administered Insulin–Like Growth Factor–I (rhIGF) (CEP–151) in Multiple Sclerosis (MS) Patients", *National Institute of Neurological Disorders and Stroke (NINDS)*.

"Retrospective Analysis of the Effects of Low Dose, High Frequency Human Growth Hormone on Serum Lipids and Prostate Antigen" by Edmund Y. Chein, MD, JD, et al. *Palm Springs Life Extension Institute Manual*, Dec. 26, 1995.

* cited by examiner

HORMONE THERAPY METHODS AND HORMONE PRODUCTS FOR ABATING CORONARY ARTERY BLOCKAGE

This invention relates to methods and products to abate coronary artery blockage in men and in women. These methods include administering a combination of natural hormones, including human growth hormone or recombinant human growth hormone, one or more sex hormones, such as testosterone, estrogen or progesterone and other naturally occurring hormones, as appropriate.

The methods and products of this invention are disclosed in part in U.S. Pat. No. 5,855,920, issued Jan. 5, 1999, entitled TOTAL HORMONE REPLACEMENT THERAPY. The entire text of the '920 patent is incorporated herein by this reference. However, in abating coronary artery blockage in men and women, the methods of this invention additionally call for administering sufficient T3 thyroid supplement to maintain the body temperature of males and females with such blockage above about 97.6° F. upon awakening, and is in the range of about 98.7° F. to about 99.0° F. during the afternoon hours. In addition, in treating males with coronary artery blockage, and with below optimal testosterone levels, these methods call for administering natural testosterone in gel form, preferably applied topically to under arm pits.

In treating a human male or female subject who has blockage of coronary arteries, a treating physician preferably obtains the subject's records, including, where available, MRI, CAT scan, angiogram and all other pictorial and visual documentation of the blockage. The treating physician then measures the subject's total cholesterol, HDL, LDL, and triglyceride levels, and the subject's hormones in terms of growth hormone level as reflected through IGF-1 level, melatonin level, thyroid hormone level, thymus hormone level, adrenal hormone of DHEA level and pregnenolone level, and the subject's sex hormone(s) level (in males, testosterone; in females, progesterone and estrogen).

In treating males or females presenting with coronary artery blockage, all of these hormones, if below optimal levels, would be administered to increase their bloodstream levels to optimal, as that term is used in the '920 patent. In addition, in male human subjects requiring testosterone supplement, testosterone would be administered in natural form, i.e. in gel form, not in synthetic form, such as testosterone types with prefixes or suffixes.

In both male and female human subjects, the hormones administered include sufficient T3 thyroid supplement, in addition to the regular T4 and T3 thyroid supplements, to insure that the subject's body temperature is at or above about 97.6° F. upon awakening, and is in the range of about 98.7° F. to about 99.0° F. during afternoon hours.

The treatment continues until the coronary artery blockage has abated, as determined by tests such as MRI, CAT scan and/or angiogram.

What is claimed is:

1. A method for abating coronary artery blockage in otherwise healthy male and female human subjects in need thereof comprising:

measuring hormone levels in a sample of the subject's blood to determine that the level of human growth hormone and the supplemental hormones selected from the group consisting of sex hormone, melatonin hormone, adrenal hormone, thyroid hormone, and thymus hormone are below predetermined optimal physiological levels for an adult human;

replenishing said level of said deficient hormones to the predetermined optimal physiological levels, without maintaining said human subject's body temperature upon awaking at or above about 97.6° F., and without maintaining said subject's body temperature in the range of about 98.7° F. to about 99.0° F. during afternoon hours;

with the additional step of administering to said human subject sufficient T3 thyroid supplement to maintain said human subject's body temperature upon awaking at or above about 97.6° F., and to maintain said subject's body temperature in the range of about 98.7° F. to about 99.0° F. during afternoon hours; and in the case of a male human subject whose natural testosterone level is below said predetermined physiological level, administering natural testosterone in gel form to effect said replenishing.

2. The method of claim 1 wherein the step of measuring the level of human growth hormone comprises measuring the level of insulin-like growth factor-I.

3. The method of claim 1 wherein the predetermined physiological level of human growth hormone is an insulin-like growth factor-I level of 350 $\mu$g./mL blood.

4. The method of claim 1, the step of replenishing said level of human growth hormone further comprising a regimen comprising subcutaneous injections of doses of less than 0.5 mg per day.

5. The method of claim 1 wherein said regimen of injections of human growth hormone are administered twice daily.

6. The method of claim 1, wherein said sex hormone comprises at least one of natural testosterone, progesterone, and estrogen.

7. The method of claim 1 wherein said adrenal hormone comprises dehydroepiandrosterone and pregnenolone.

8. The method of claim 1, in the step of measuring a sample of a human subject's blood, further comprising determining whether each of the supplemental hormones are below predetermined physiological levels for an adult human.

9. The method of claim 8 wherein the predetermined physiological level per milliliter of blood of human growth hormone is an insulin-like growth factor-I level of 350 $\mu$g, the level of melatonin hormone is 18–69 $\mu$g, and the level of thyroid (T3) hormone is 150–180 $\mu$g.

* * * * *